United States Patent
Shin et al.

(10) Patent No.: US 7,906,676 B2
(45) Date of Patent: Mar. 15, 2011

(54) PROCESS FOR PREPARING 3-AMINO-5-FLUORO-4-DIALKOXYPENTANOIC ACID ESTER

(75) Inventors: Hyun Ik Shin, Daejeon (KR); Hyeong Wook Choi, Daejeon (KR); Jae Hoon Lee, Daejeon (KR); Kyu Woong Lee, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 173 days.

(21) Appl. No.: 12/376,424

(22) PCT Filed: Aug. 9, 2007

(86) PCT No.: PCT/KR2007/003822
§ 371 (c)(1),
(2), (4) Date: Feb. 17, 2009

(87) PCT Pub. No.: WO2008/020691
PCT Pub. Date: Feb. 21, 2008

(65) Prior Publication Data
US 2010/0036158 A1    Feb. 11, 2010

(30) Foreign Application Priority Data
Aug. 16, 2006   (KR) .................. 10-2006-0077360

(51) Int. Cl.
*C07C 229/00*    (2006.01)
*C07C 69/73*    (2006.01)
*C07C 69/66*    (2006.01)

(52) U.S. Cl. .......... 560/170; 560/172; 560/183; 560/184
(58) Field of Classification Search .............. None
See application file for complete search history.

(56) References Cited

U.S. PATENT DOCUMENTS
6,153,591 A * 11/2000 Cai et al. ............... 514/19
6,200,969 B1 * 3/2001 Fritz et al. ............ 514/212.05
6,566,338 B1 * 5/2003 Weber et al. ............ 514/19

FOREIGN PATENT DOCUMENTS
WO    WO-99/47154 A1    9/1999
* cited by examiner

*Primary Examiner* — Karl J Puttlitz
(74) *Attorney, Agent, or Firm* — Birch, Stewart, Kolasch & Birch, LLP

(57) ABSTRACT

The present invention relates to a novel process for the production of 3-amino-5-fluoro-4-dialkoxypentanoic acid ester used in the precursor of 3-amino-5-fluoro-4-oxopentanoic acid, represented by the following formula (I): wherein R1 and R2 are as defined in the Description.

$$\begin{array}{c} R^2O \quad OR^2 \\ H_2N \underset{CO_2R^1}{\diagdown} F \end{array} \quad (I)$$

18 Claims, No Drawings

PROCESS FOR PREPARING 3-AMINO-5-FLUORO-4-DIALKOXYPENTANOIC ACID ESTER

FIELD OF THE INVENTION

The present invention relates to a novel process for the production of 3-amino-5-fluoro-4-dialkoxypentanoic acid ester represented by the following formula 1:

[Formula 1]

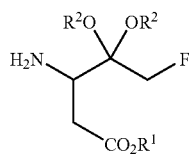

wherein $R^1$ and $R^2$ are as defined below.

BACKGROUND ART

Revesz group reported a process for the production of 3-amino-5-fluoro-4-oxopentanoic acid derivative which is well known in the art to play an important role in caspase inhibitor (Revesz et al., *Tetrahedron Lett.* 1994, 35, 9693). However, this process used an intermediate 2-fluoroacetaldehyde that is volatile, and its aldol reaction requires a large amount of organic solvent. Moreover, the purification of the product is difficult since there is no intermediate obtained as the form of solid. To overcome these problems, the present inventors developed a process of Reaction Scheme 1 for preparing the compound of formula 1 which is practical and provides good yield (see: KR 10-2005-016203).

[Reaction Scheme 1]

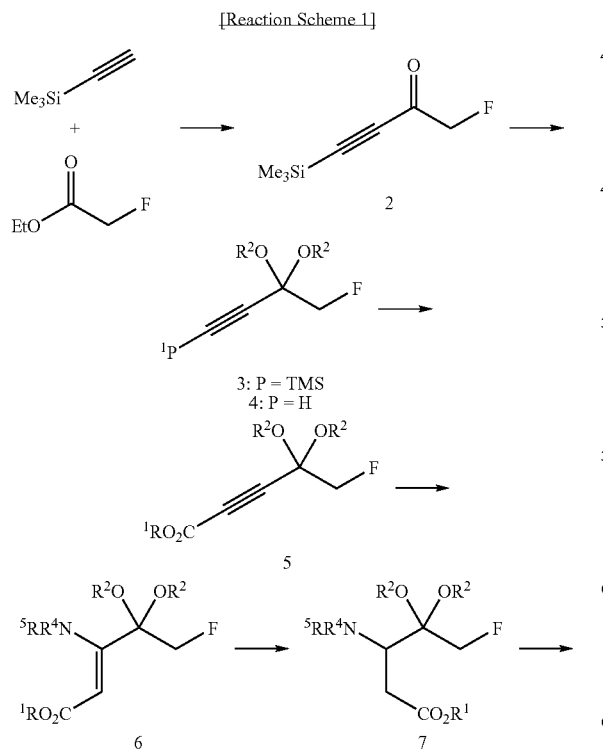

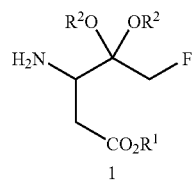

Although significant improvement was made compared to the Revesz's process, there is still room for further refinements in removing a very low temperature condition in preparing a compound of formula 2 by condensation between lithium anion of trimethylsilyl acetylene and ethylfluoroacetate, and in preparing a compound of formula 5 by condensation between anion of a compound of formula 4 and ethyl chloroformate (−25° C.~−65° C., and below −40° C., respectively). Furthermore, the intermediates obtained from the above Reaction Scheme could not be purified easily, and so the above method was difficult to be used for synthesizing the compounds in a large scale. Therefore, there has been a need for a new method which does not require the very low temperature condition, and has an easy purification process.

SUMMARY OF THE INVENTION

The present invention relates to a novel process for the production of 3-amino-5-fluoro-4-dialkoxypentanoic acid ester used in the precursor of 3-amino-5-fluoro-4-oxopentanoic acid, represented by the following formula 1:

[Formula 1]

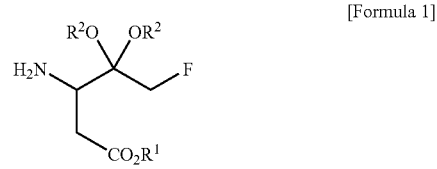

wherein $R^1$ and $R^2$ are as defined in the Description.

DETAILED DESCRIPTION OF THE INVENTION

The object of the present invention is to provide a process for preparing a compound of formula 1 which does not require a very low temperature condition, and is suitable for a large scale of synthesis in which intermediates can be easily purified.

The present invention relates to a process for producing a compound of formula 6, which comprises the following steps:
(a) preparing a compound of formula 4 by deprotecting a compound of formula 3;
(b) preparing a compound of formula 9 by reacting the compound of formula 4 with $R^1OC(=O)OR^3$; and,
(c) reacting the compound of formula 9 with $NH(R^4)(R^5)$:

[Formula 3]

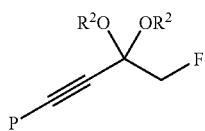

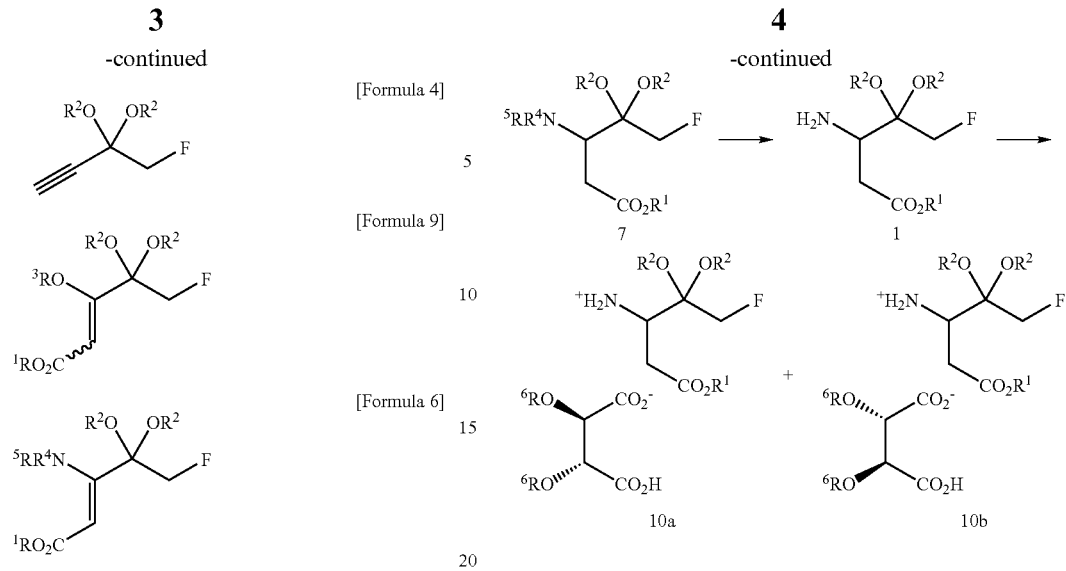

in which,

R¹ and R³ independently represent alkyl group;

R² independently represents alkyl group, or together with the oxygen atom to which they are attached may form a dioxolane or dioxane;

R⁴ and R⁵ independently represent hydrogen, trialkylsilyl group, arylmethyl group, or 1-arylethyl group, and, P represents protecting group.

Also, the present invention relates to a method for producing the compound of formula 1, including the above method. When using the process of the present invention, the very low temperature condition is not required, and the purification process is simple. The reaction mechanism of the present invention can be depicted in the following Reaction Scheme 2:

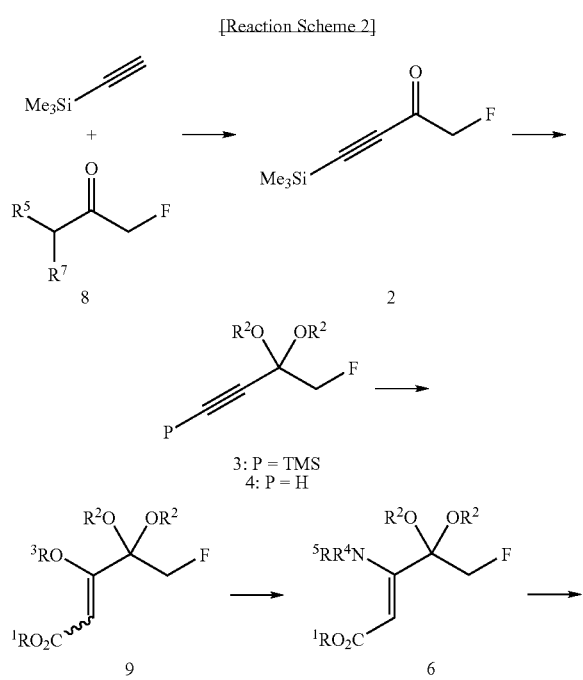

In the Reaction Scheme 2, the method for producing the compound of formula 2 by using the condensation reaction between an amide compound of formula 8 and trimethylsilyl acetylene, and the method for preparing a compound of formula 6 from a compound of formula 9 via the compound of formula 4 do not require a very low temperature condition. Also, the crystallized solid form of compounds of formulae 6, 10a, and 10b can be obtained by the above process, and so the compound of formula 1 can be obtained in high purity. Furthermore, the compound of formula 9 is a new compound.

The present invention may be explained in light of the following examples in more detail. However, they are set forth for the purpose of illustration, and cannot be construed to limit the present invention in any manner.

DEFINITIONS

In describing the compounds and methods of the present invention, main terms have the following meanings unless indicated otherwise.

The term, "alkyl," means $C_{1-8}$-hydrocarbon radicals, or $C_{3-10}$-cyclic hydrocarbon radicals which may be linear or branched, and so may be methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, cyclopropyl, cyclobutyl, cyclopentyl, cyclohexyl, cycloheptyl, cyclooctyl and the like, but are not limited thereto.

The term, "aryl," means aromatic group, heteroaromatic group, or partially reduced derivatives thereof. Aromatic group refers to 5-15 membered, unsaturated hydrocarbons which may be unfused ring or fused ring. Aromatic group includes benzene, biphenyl, naphthalene and the like, but are not limited thereto. The above heteroaromatic group is 5-15 membered aromatic group having 1 to 5 hetero atoms selected from the group consisting of oxygen, sulfur, and nitrogen, which may be unfused ring or fused ring. Monocyclic heteroaromatic group includes thiazole, oxazole, thiophene, furan, pyrrole, imidazole, isoxazole, pyrazole, triazole, thiadiazole, tetrazole, oxadiazole, pyridine, pyridazine, pyrimidine, pyrazine and the like, but are not limited thereto. Bicyclic heteroaromatic group includes indole, benzothiophene, benzofuran, benzimidazole, benzoxazole, benzisoxazole, benzthiazole, benzthiadiazole, benztriazole, quinoline, isoquinoline, purine, furopyridine and the like, but are not limited thereto.

The term, "heterocycle," means a saturated 4-8 membered ring or 4-8 membered ring having 1 or 2 double bonds which may be fused with benzo or $C_3$-$C_8$-cycloalkyl, and includes 1 or 2 hetero atoms selected from the group consisting of oxygen, sulfur and nitrogen. Heterocycle includes piperidine, morpholine, thiamorpholine, pyrrolidine, imidazolidine, tetrahydrofuran, piperazine and the like, but are not limited thereto.

Here, one or more hydrogen of the alkyl group and aryl group can be substituted by other substituents, including acyl, amino, carboalkoxy, carboxy, carboxyamino, cyano, halo, hydroxy, nitro, thio, alkyl, cycloalkyl, alkoxy, aryl, aryloxy, sulfoxy and guanido group, but are not limited thereto.

Synthesis of a Compound of Formula 2

As shown in the Reaction Scheme 3, the compound of formula 2 is obtained through the steps of:
(i) preparing a compound of formula 8 by reacting A-OC(=O)$CH_2$F with NH($R^6$)($R^7$); and,
(ii) reacting the compound of formula 8 with trimethylsilyl acetylene.

The above reaction does not require a very low temperature condition.

[Reaction Scheme 3]

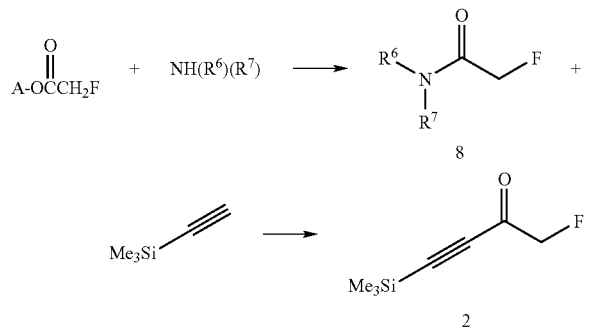

wherein,
A represents alkyl, such as hydrogen, ethyl, methyl; or metal, such as sodium;
$R^6$ and $R^7$ independently represent substituted or unsubstituted alkyl, such as methyl, phenylmethyl; or substituted or unsubstituted alkoxy, such as methoxy, phenylmethoxy; or together with the nitrogen atom to which they are attached may form a 4-8 membered heterocycle, such as morpholine.

In the step (i), the amide compound of formula 8 is obtained by condensation between fluoroacetic acid and NH($R^6$)($R^7$), preferably N,O-dimethylhydroxyamine or morpholine. It is desirable that the condensation reaction is carried out after activating A-OC(=O)$CH_2$F by dicyclohexyl carbodiimide or N-(3-dimethylaminopropyl)-N'-ethylcarbodiimide hydrochloride (EDC).

In case the condensation uses morpholine, the compound of formula 8 can be easily obtained by reacting morpholine with an ester of fluoroacetic acid comprising ethyl fluoroacetate and methyl fluoroacetate without condensation reagent. The amount of NH($R^6$)($R^7$) used in the reaction is 1.5 to 5 equivalents, preferably 1.5 to 3 equivalents, with respect to the A-OC(=O)$CH_2$F. If the amount of NH($R^6$)($R^7$) is below 1.5 equivalents, the reaction speed slows down, and if the amount is excess 5 equivalents, the removal of excess amine is difficult. Preferably, the condensation reaction is conducted under the presence of one or more solvents selected from the group consisting of toluene and acetonitrile, but is not limited thereto. It is more preferable for the reaction to be conducted in the absence of solvent in terms of the reaction speed. The reaction temperature is preferably 60° C. to 100° C., more preferably 65° C. to 90° C. If the reaction temperature is below 60° C., the reaction speed is slow, and if it is over 100° C., the yield is reduced by side reaction.

For the step (ii), the compound of formula 8 can be used without limitation. However, in a large scale of synthesis, it is preferable to use the compound of formula 8 which includes morpholine ring together with the nitrogen atom to which $R^6$ and $R^7$ are attached, in terms of stability and economy. The amount of trimethylsilylacetylene is 1 to 3 equivalents, preferably 1.1 to 1.5 equivalents, with respect to the compound of formula 8. If the amount of trimethylsilylacetylene is over 3 equivalents, a large amount of by-product reacting with 2 molecules of trimethylsilylacetylene is synthesized. It is preferable to use lithium trimethylsilylacetylide that is converted from trimethylsilylacetylene by using alkyllithium, preferably methyl lithium, n-hexyl lithium, or n-butyl lithium. The reaction is preferably carried out under the presence of one or more solvents selected from the group consisting of tetrahydrofuran, diethylether, t-butylmethylether and 1,2-dimethoxyethane, though not specially limited thereto, as long as there is no negative effect to the reaction. The reaction temperature is −30° C. to 20° C., preferably −10° C. to 20° C.

Synthesis of a Compound of Formula 4

The compound of formula 4 is prepared by reacting the compound of formula 2 with a protecting group, to obtain a compound of formula 3 (as shown in the Reaction Scheme 4 below), and deprotecting the compound of formula 3.

[Reaction Scheme 4]

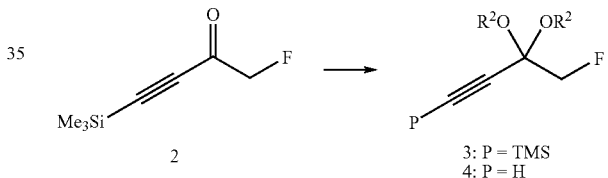

wherein,
$R^2$ independently represents alkyl group, or together with the oxygen atom to which they are attached may form a dioxolane or dioxane.

For the above protecting reaction, a trialkylorthoformate is used in the methanol or ethanol solvent. Preferably, trimethylorthoformate or triethylorthoformate is used, but is not limited thereto. The protecting reaction is preferably carried out under the presence of one or more bases selected from the group consisting of $M^1$OH, $M^2$(OH)$_2$, ($M^1$)$_2$CO$_3$, ($M^1$)HCO$_3$ and $M^2$CO$_3$, preferably sodium hydroxide, potassium hydroxide, sodium carbonate and sodium hydrogen carbonate, wherein $M^1$ represents alkali metal, $M^2$ represents alkaline earth metal. The amount of the base used in the deprotecting reaction is 1 to 2 equivalents with respect to the compound of formula 2.

Also, it is preferable to carry out the deprotecting reaction in $C_1$-$C_8$ alcohol, such as methanol or ethanol; dichloromethane; or a mixture of chloroform and water.

Synthesis of a Compound of Formula 9

The compound of formula 9 is prepared by reacting the compound of formula 4 with $R^1$OC(=O)OR$^3$ (as shown in the Reaction Scheme 5 below). The reaction is preferably conducted under the presence of base. The compound of formula 9 obtained from the reaction is new compound.

[Reaction Scheme 5]

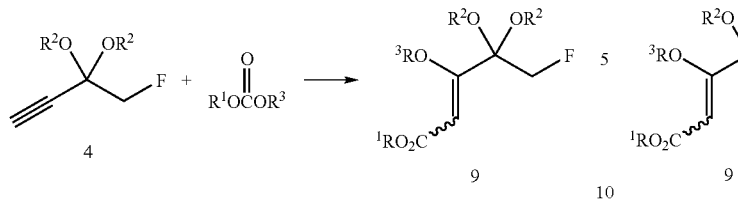

wherein, $R^1$ and $R^3$ independently represent alkyl group;

$R^2$ independently represents alkyl group, or together with the oxygen atom to which they are attached may form a dioxolane or dioxane.

The bases used in the reaction are not limited, as long as the compound of formula 4 can react with $R^1OC(=O)OR^3$, and the bases are preferably alkali metal; primary, secondary or tertiary alkoxide of alkaline earth metal; Grignard reagent; alkyllithium; lithium dialkylamide; lithium hexamethylsilazide; sodium hexamethylsilazide; or potassium hexamethylsilazide. The amount of the base used herein is 0.05 to 1.5 equivalent, preferably 0.1 to 0.5 equivalent, with respect to the compound of formula 4. If the amount of the base used is below 0.05 equivalent, the reaction speed slows down, and if it is over 1.5 equivalents, two (2) molecules of the compound of formula 4 react with one molecule of $R^1OC(=O)OR^3$, to obtain unwanted by-product.

The preferable compound of $R^1OC(=O)OR^3$ is one that $R^1$ and $R^3$ are independently selected from the group consisting of methyl, ethyl, propyl, butyl and isopropyl. The more preferable compound of $R^1OC(=O)OR^3$ is dimethyl carbonate, diethyl carbonate, dipropyl carbonate, dibutyl carbonate or diisopropyl carbonate, but is not limited thereto. The amount of $R^1OC(=O)OR^3$ used is 1 to 5 equivalents, preferably 1 to 2.5 equivalents, more preferably 1.05 to 1.15 equivalents, with respect to the compound of formula 4. If the amount of $R^1OC(=O)OR^3$ used is over 5 equivalents, the reaction slows down, and cannot be completed.

As long as the reaction solvent has no negative effect, it is not specially limited, but the reaction solvent includes one or more solvents selected from the group consisting of dimethylformamide, dimethylsulfoxide and N-methylpyrrolidinone, or a mixture thereof with tetrahydrofuran. However, it is not preferable to use tetrahydrofuran alone as the reaction solvent in terms of the reaction speed. The amount of reaction solvent is not specially limited, but is more than 5 times, preferably 10 times, based on the amount of $R^1OC(=O)OR^3$. If the amount of the reaction solvent is less than 5 times, the reaction speed slows down.

The reaction temperature is −20° C. to 50° C., preferably −5° C. to 30° C. If the temperature is over 50° C., the yield decreases.

The compound of formula 9 obtained from the Reaction Scheme 2 is a mixture of E and Z, and the ratio of E and Z is varied depending on the reaction condition. However, both of these isomers can be reacted with amine to obtain the compound of formula 6, and so no isolation process is required.

Synthesis of a Compound of Formula 6

A compound of formula 6 is prepared by reacting the compound of formula 9 with $NH(R^4)(R^5)$, as shown in the Reaction Scheme 6 below.

[Reaction Scheme 6]

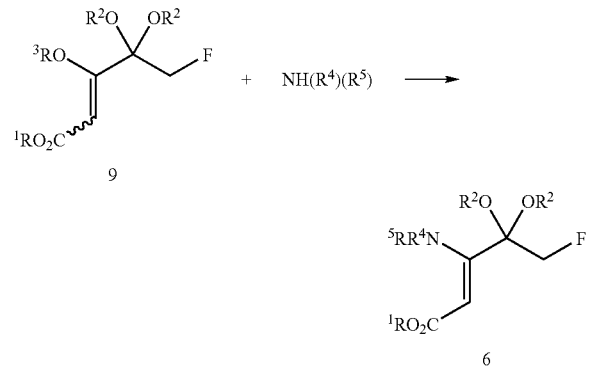

wherein, $R^1$ and $R^3$ independently represent alkyl group;

$R^2$ independently represents alkyl group, or together with the oxygen atom to which they are attached may form a dioxolane or dioxane;

$R^4$ and $R^5$ independently represent hydrogen, trialkylsilyl group, arylmethyl group or 1-arylethyl group.

$NH(R^4)(R^5)$ used herein is not specially limited as long as it can be converted to amino group by reduction, but preferably arylmethylamine such as ammonia or benzylamine; primary amine including 1-arylethylamine, such as 1-phenylethylamine or 1-naphthylethylamine, or protected trialkylsilyl form thereof; and secondary amine including di(arylmethyl)amine, such as dibenzylamine, or di(arylethyl)amine such as diphenylethylamine. The amount of $NH(R^4)(R^5)$ is 1 to 20 equivalents, preferably 3 to 8 equivalents. If the amount of $NH(R^4)(R^5)$ is less than 1 equivalent, the reaction speed slows down. If it is over 20 equivalents, it is disadvantageous in that an excess amount of acid should be used to remove amine produced after the reaction.

The reaction is not specially limited, as long as the solvent has no negative effect to the reaction, but preferably is carried out under the presence of the solvent selected from the group consisting of t-butylmethylether, toluene, dimethylformamide and acetonitrile. It is more preferable to be carried out in the absence of solvent in terms of reaction speed. The reaction temperature is from 30° C. to 150° C., preferably from 80° C. to 110° C. If the reaction temperature is below 30° C., it is disadvantageous in terms of the reaction rate. If it is over 150° C., the side reaction is problematic.

The product obtained from the reaction can be used for the next reaction after removing excess amine. However, the compound of formula 6 is preferably purified via crystallization to prepare the compound of formula 1 in high purity. The resulting product obtained from removing amine is heated and dissolved in one or more solvents, preferably selected from the group consisting of methanol, ethanol, isopropanol and acetone, and water is added thereto, to cause the compound of formula 6 to begin crystallization. Additional process of purification such as recrystallization is not required since the resulting precipitation includes the compound of formula 6 in high purity.

Synthesis of a Compound of Formula 7

A compound of formula 7 is prepared by reducing under the presence of the reducing agent capable of selectively reducing the double bond between carbons existing in the compound of formula 6, as shown in the following Reaction Scheme 7.

[Reaction scheme 7]

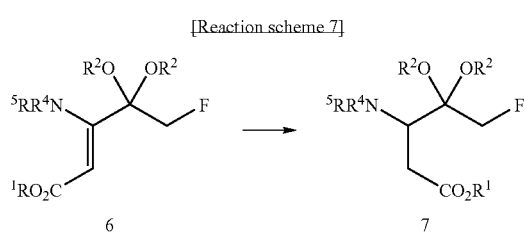

wherein,

R$^1$ independently represents alkyl group;
R$^2$ independently represents alkyl group, or together with the oxygen atom to which they are attached may form a dioxolane or dioxane;
R$^4$ and R$^5$ independently represent hydrogen, trialkylsilyl group, arylmethyl group or 1-arylethyl group.

As long as the reducing agent has no negative effect to the reduction reaction, conventional reducing agent capable of selectively reducing the double bond between carbon and nitrogen can be used in the reaction. Preferably, (i) sodium triacetoxyborohydride; (ii) acetic acid and sodium cyanoborohydride; or (iii) acetic acid and sodium borohydride, can be used, but is not limited thereto. The amount of reducing agent is from 1 to 5 equivalents, preferably 1.5 to 3 equivalents, with respect to the compound of formula 6. If the amount of reducing agent is less than 1 equivalent, the reaction cannot be completed. If it is more than 5 equivalents, it may be dangerous since excess hydrogen gas is produced from excess reducing agent when the reaction is quenched by water. In case of using acetic acid and sodium borohydride as the reducing agent, it is preferable to use each of them from 1 to 20 equivalents and from 1 to 5 equivalents, respectively. It is also preferable to conduct the reaction under the presence of one or more solvents selected from the group consisting of ethylacetate, tetrahydrofuran, diethylether and t-butylmethylether.

Synthesis of a Compound of Formula 1

The compound of formula 1 is prepared by hydrogenating the compound of formula 7 as shown in the following Reaction Scheme 8 below.

[Reaction Scheme 8]

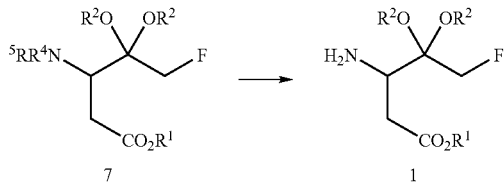

wherein,

R$^1$ independently represents alkyl group;
R$^2$ independently represents alkyl group, or together with the oxygen atom to which they are attached may form a dioxolane or dioxane;
R$^4$ and R$^5$ independently represent hydrogen, trialkylsilyl group, arylmethyl group or 1-arylethyl group.

The reaction is conducted under the presence of metal catalyst, preferably palladium based catalyst or Raney nickel based catalyst, which is not limited thereto, but the palladium based catalyst having palladium(Pd) loading range of from 1 to 20 weight % or Raney nickel based catalyst having nickel loading range of more than 1 weight % can be used in an amount of from 0.01 to 13 weight % to the compound of formula 7, based on the metal component, wherein said catalysts are in a loaded form into the support selected from the group consisting of carbon, silica, and alumina. The hydrogenation reaction is not limited, but preferably is conducted under the presence of one or more solvents selected from the group consisting of acetic acid, methanol, ethanol, n-propanol, isopropanol, tetrahydrofuran, dimethoxyethane, dioxane, ethylacetate and dichloromethane. Also, the hydrogenation reaction is preferably conducted under from 0 to 50° C., and 1 to 100 atmospheres of hydrogen pressure.

Synthesis of a Compound of Formula 10, and Purification and Optical Resolution of the Compound of Formula 10 Used Thereof A compound of formula 10 (isomers of formula 10a, stereoisomers of formula 10b, or racemates of formula 10a and formula 10b) is prepared by reacting the compound of formula 1 with tartaric acid derivatives (if necessary, racemates or optical isomers), as shown in the Reaction Scheme 9 below. The resulting compound of formula 10 can be used for the purification and optical resolution process of the compound of formula 1.

[Reaction Scheme 9]

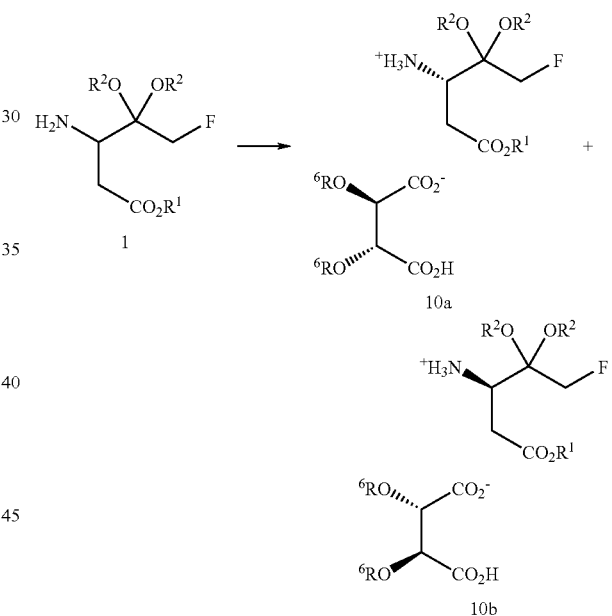

wherein,

R$^1$ independently represents alkyl group;
R$^2$ independently represents alkyl group, or together with the oxygen atom to which they are attached may form a dioxolane or dioxane;
R$^6$ represents hydrogen, alkyl group or acyl group, wherein acyl has the form of RC(=O)—,
wherein R is alkyl group or aryl group.

The compound of formula 1 reacts with tartaric acid derivatives in the presence of water, and one or more solvents selected from C$_1$-C$_5$-alcohol, preferably, selected from the group consisting of methanol, ethanol and isopropanol, to obtain the compound of formula 10 (stereoisomers of formula 10a, stereoisomers of formula 10b, or racemic mixture of formula 10a and formula 10b). The reaction is conducted preferably in the temperature range of from 40° C. to 80° C. After the reaction is completed, if the temperature of the reactant cools down to a low temperature, preferably below ambient temperature, the compound of formula 10 is crystallized. The resulting precipitates include the compound of formula 10 having sufficient purity. However, if necessary, the compound of formula 10 having higher purity can be obtained from recrystallization in the presence of water and one or more solvents selected from $C_1$-$C_5$-alcohol group, preferably selected from the group consisting of methanol, ethanol and isopropanol.

The amount of tartaric acid derivatives used is 0.9 to 1.5 equivalents with respect to the compound of formula 1.

Tartaric acid derivatives used in the reaction preferably include tartaric acid, O,O'-dibenzoyltartaric acid and the like, but are not limited thereto.

The compound of formula 10 can be easily isolated to the compound of formula 1 and tartaric acid derivatives by using the conventional method which isolates salt from the compound. Thus, the compound of formula 1 can be isolated in high purity. If the racemates or enantiomers of the compound of formula 1 are required, the racemic mixture of formula 10a and formula 10b, the stereoisomers of formula 10a, or the stereoisomers of formula 10b are prepared by selectively using racemic tartaric acid derivatives or tartaric acid derivatives having optical activity. In particular, in case of using tartaric acid derivatives having optical activity, the compound of formula 1 can be optically divided since one enantiomer of the compound of formula 1 can form diastereomeric salt of formula 10a or 10b. The tartaric acid derivatives having optical activity used in the reaction include optically active tartaric acid such as D,L-tartaric acid, O,O'-dibenzoyltartaric acid, but are not limited thereto.

Better understanding on the present invention may be obtained in light of the following examples which are set forth to for the purpose of illustration, which however cannot be construed to limit the present invention in any way.

ADVANTAGEOUS EFFECTS

The present invention provides advantages over the known prior arts since it the does not require a very low temperature condition, and the intermediate 6 is easily purified via crystallization to provide high purity of the compound of formula 1.

BEST MODE

The present invention relates to a process for producing a compound of formula 6 described below, which comprises the following steps:

(a) preparing a compound of formula 4 described below by deprotecting a compound of formula 3 described below;

(b) preparing a compound of formula 9 described below by reacting the compound of formula 4 with $R^1OC(=O)OR^3$; and (c) reacting the compound of formula 9 with $NH(R^4)(R^5)$:

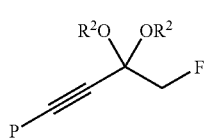

[Formula 3]

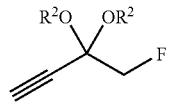

[Formula 4]

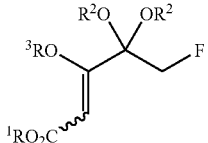

[Formula 9]

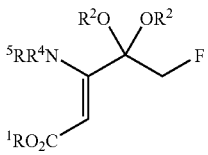

[Formula 6]

in which, $R^1$ and $R^3$ independently represent alkyl group;

$R^2$ independently represents alkyl group, or together with the oxygen atom to which they are attached may form a dioxolane or dioxane;

$R^4$ and $R^5$ independently represent hydrogen, trialkylsilyl group, arylmethyl group or 1-arylethyl group, and P represents protecting group.

MODE FOR INVENTION

Example 1

2-Fluoro-1-morpholin-4-yl-ethanone (8)

A mixture of ethyl fluoroacetate (50 g, 472 mmol) and morpholine (82 g, 944 mmol) was heated at 70° C. for 20 h. After cooling to ambient temperature, the mixture was added to a stirred mixture of 2 N HCl (240 mL) and methylene chloride (200 mL) over 20 min. The organic layer was separated and the aqueous layer was extracted with dichloromethane (200 mL×2). The combined organic phase was dried over anhydrous $MgSO_4$ and concentrated in vacuo to give 51.7 g (74.6%) of the title compound. $^1$H NMR (400 MHz, $CDCl_3$) δ 4.96 (d, J=47.2 Hz, 2H), 3.70 (bs, 4H), 3.64 (bs, 2H), 3.47 (bs, 2H).

Example 2

1-Fluoro-4-trimethylsilanyl-but-3-yn-2-one (2)

A 0° C. solution of trimethylsilylacetylene (42.0 g, 429 mmol) in THF (400 mL) was treated with n-BuLi (2.5 M in n-hexane; 171 mL, 428 mmol) over 20 min maintaining the internal temperature below 10° C. using dry ice-acetone bath (−20° C.). After stirring for 30 min at 0° C., the mixture was treated with a solution of 2-fluoro-1-morpholin-4-yl-ethanone (8, 48.4 g, 329 mmol) in THF (50 mL+10 mL for wash), and stirring was continued for further 1 h at 0° C. The reaction was quenched by adding to a 0° C. mixture of acetic acid (250 mL) and water (150 mL) over 1 h maintaining the internal temperature below 5° C. After addition of more water (150 mL), the organic layer was separated, washed with water (200 mL), and dried over anhydrous $MgSO_4$, and concentrated in vacuo. The residue was evaporated again with toluene (200 mL) to remove the residual acetic acid, and vacuum distillated (8 mbar, b.p. 54° C.) to give the title compound (33.7 g, 64.8%). $^1$H NMR (500 MHz, CDCl$_3$) δ 4.90 (d, J=47.1 Hz, 2H), 0.26 (s, 9H). $^{13}$C NMR (125 MHz, CDCl$_3$) d 181.0 (d, J=21.5 Hz), 104.0, 98.1, 84.8 (d, J=187 Hz).

Example 3

4-Fluoro-3,3-dimethoxy-but-1-yne (4, R$^2$=methyl)

A solution of 1-fluoro-4-trimethylsilanyl-but-3-yn-2-one (2, 50.0 g, 316 mmol) in methanol (260 mL) was treated with trimethyl orthoformate (33.6 g, 316 mmol) and p-TsOH—H$_2$O (6.0 g, 31.5 mmol), and refluxed (bath temperature: 80° C.) for 6 h. After evaporation of about 130 mL of solvent under reduced pressure, the residue was diluted with dichloromethane (260 mL) and 10% NaHCO$_3$ solution (130 mL). The organic layer was separated and the aqueous layer was extracted with dichloromethane (130 mL). The organic phases were combined and concentrated under reduced pressure to give a crude compound of formula 3 (59.0 g, 92%). The compound was used as such for the next reaction. $^1$H NMR (500 MHz, CDCl$_3$): δ 4.38 (d, J=47.1 Hz, 2H), 3.40 (s, 6H), 0.20 (s, 9H).

To a solution of a crude compound of formula 3 (59.0 g, 289 mmol) in dichloromethane (280 mL) was added tetra-n-butylammonium bromide (59 mg, 0.183 mmol) and 1 N NaOH (347 mL, 347 mmol). The mixture was stirred at ambient temperature for 2 h. The organic layer was separated and the aqueous layer was extracted with dichloromethane (110 mL). The combined organic phase was washed with brine (110 mL) and concentrated under reduced pressure to give a crude the title compound (4, R$^2$=methyl, 40.9 g, 107%). $^1$H NMR (500 MHz, CDCl$_3$): δ 4.42 (d, J=47.1 Hz, 2H), 3.42 (s, 6H), 2.64 (s, 1H). $^{13}$C NMR (125 MHz, CDCl$_3$) δ 96.1 (d, J=20.3 Hz), 82.9 (d, J=180 Hz), 77.5, 75.5, 51.0.

Example 4 ethyl 3-ethoxy-5-fluoro-4,4-dimethoxypent-2-enoate (9, R$^1$ and R$^3$=ethyl, R$^2$=methyl)

A mixture of 4-fluoro-3,3-dimethoxy-but-1-yne (4, R$^2$=methyl, 20.0 g, 152 mmol) and diethyl carbonate (20.1 mL, 167 mmol) in DMF (150 mL) was cooled to 0° C., and treated with potassium ethoxide (3.8 g, 45.2 mmol). After stirring at 0° C. for 4 h, the solution was charged with a 1:1 mixture of saturated aqueous NH$_4$Cl and water (200 mL) and extracted with t-butylmethylether (200 mL×2). The combined organic phase was washed with water (100 mL) and dried over anhydrous MgSO$_4$ to give a crude the title compound (9, R$^1$ and R$^3$=ethyl, R$^2$=methyl, 37.8 g, 99.7%, Z:E=6.5:1). (Z)-isomer: $^1$H NMR (400 MHz, CDCl$_3$) δ 5.84 (s, 1H), 4.48 (d, J=46.8 Hz, 2H), 4.27 (q, J=7.2 Hz, 2H), 4.17 (q, J=7.2 Hz, 2H), 3.26 (s, 6H), 1.32 (t, J=7.2 Hz, 3H), 1.28 (t, J=7.2 Hz, 3H). $^{13}$C NMR (100 MHz, CDCl$_3$) δ 164.9, 162.5, 100.7, 99.2 (d, J=30 Hz), 78.5 (d, J=180 Hz), 70.7, 59.7, 48.9, 15.3, 14.0. (E)-isomer: $^1$H NMR (400 MHz, CDCl$_3$) δ 5.21 (s, 1H), 4.59 (d, J=46.8 Hz, 2H), 4.16 (q, J=7.2 Hz, 2H), 3.82 (q, J=7.2 Hz, 2H), 3.29 (s, 6H), 1.35 (t, J=7.2 Hz, 3H), 1.29 (t, J=7.2 Hz, 3H). $^{13}$C NMR (100 MHz, CDCl$_3$) δ 167.2, 157.3, 99.8 (d, J=20 Hz), 97.6, 80.6 (d, J=180 Hz), 64.0, 60.2, 49.4, 14.0.

Example 5

(Z)-ethyl 3-benzylamino-5-fluoro-4,4-dimethoxy-pent-2-enoate (6, R$^1$=ethyl, R$^2$=methyl, R$^4$=benzyl, R$^5$=hydrogen)

A mixture of ethyl 3-ethoxy-5-fluoro-4,4-dimethoxypent-2-enoate (9, R$^1$ and R$^3$=ethyl, R$^2$=methyl, 37.8 g, 151 mmol) and benzylamine (99 mL, 907 mmol) was heated to 100° C. for 20 h. After cooling to 0° C., the mixture was diluted with ethyl acetate (300 mL), and treated with 1 N HCl (360 mL) over 30 min maintaining the internal temperature below 20° C. The separated organic layer was treated with 1 N HCl (330 mL), of which pH was adjusted to ca. 4. The organic layer was separated, washed with saturated aqueous NH$_4$Cl (60 mL), dried over anhydrous MgSO$_4$, and concentrated in vacuo. The residue was dissolved in ethanol (150 mL) by heating to 80° C. and treated with water (70 mL). After removal of oil bath, the mixture was stirred for 4 h at ambient temperature and for more 1 h at 0° C. The resulting precipitate was filtered, washed with a 2:1 mixture of ethanol and water (120 mL), and dried over nitrogen purge to give the title compound (6, R$^1$=ethyl, R$^2$=methyl, R$^4$=benzyl, R$^5$=hydrogen, 30.2 g, 64.0% for two steps from the compound formula 4). $^1$H NMR (500 MHz, CDCl$_3$) δ 8.53 (bs, 1H), 7.33 (m, 5H), 5.07 (s, 1H), 4.64 (d, J=5.5 Hz, 2H), 4.48 (d, J=46.5 Hz, 2H), 4.10 (q, J=7.4 Hz, 2H), 3.30 (s, 6H), 1.25 (t, J=7.4 Hz, 3H).

Example 6

Ethyl 3-(benzylamino)-5-fluoro-4,4-dimethoxypentanoate (7, R$^1$=ethyl, R$^2$=methyl, R$^4$=benzyl, R$^5$=hydrogen)

To a cooled solution of (Z)-ethyl 3-benzylamino-5-fluoro-4,4-dimethoxypent-2-enoate (6, R$^1$=ethyl, R$^2$=methyl, R$^4$=benzyl, R$^5$=hydrogen; 30.2 g, 97 mmol) in t-butylmethylether (97 mL) was added sodium borohydride (NaBH$_4$; 7.34 g, 194 mmol) and acetic acid (58 g, 970 mmol) for 30 minutes maintaining the temperature of the mixture below 0° C. After 30 min, aqueous 3 N NaOH solution (194 mL, 582 mmol) was added thereto slowly for 30 min. The organic layer was separated, washed with brine (97 mL), and concentrated under reduced pressure to give the title compound (7, R$^1$=ethyl, R$^2$=methyl, R$^4$=benzyl, R$^5$=hydrogen, 32.1 g, 106%), which was used in the next reaction. $^1$H NMR (400 MHz, CDCl$_3$) δ 7.35-7.21 (m, 5H), 4.53 (2dd, J=46.8, 10.4 Hz, 2H), 4.13 (q, J=7.2 Hz, 2H), 3.80 (2d, J=12.8 Hz, 2H), 3.53 (dd, J=8.4, 4.0 Hz, 1H), 3.30 (s, 3H), 3.22 (s, 3H), 2.79 (dd, J=15.6, 3.6 Hz, 1H), 2.40 (ddd, J=15.6, 8.0, 1.6 Hz, 1H), 1.25 (t, J=7.2 Hz, 3H).

Example 7

Ethyl 3-amino-5-fluoro-4,4-dimethoxypentanoate (1, R$^1$=ethyl, R$^2$=methyl)

A solution of ethyl 3-(benzylamino)-5-fluoro-4,4-dimethoxypentanoate (7, R$^1$=ethyl, R$^2$=methyl, R$^4$=benzyl, R$^5$=hydrogen, 32.1 g, 103 mmol) in methanol (321 mL) was treated with 10% palladium catalyst (10% Pd/C) under hydrogen atmosphere (1 atm) for 4 h. The crude mixture was filtered through a pad of Celite® (96 g), washed with methanol (160 mL), and the filtrate was concentrated under reduced pressure to give the title compound (1, R$^1$=ethyl, R$^2$=methyl, 21.4 g, 94%), which was used in the next reaction.

$^1$H NMR (500 MHz, CDCl$_3$) δ 4.53 (2dd, J=46.5, 10.4 Hz, 2H), 4.14 (q, J=7.3 Hz, 2H), 3.57 (dd, J=11.0, 1.9 Hz, 1H), 3.29 (d, J=11.7 Hz, 6H), 2.73 (dd, J=16.5, 2.5 Hz, 1H), 2.36 (ddd, J=16.5, 10.4, 2.5 Hz, 1H), 1.25 (t, J=7.3 Hz, 3H).

Example 8

1-ethoxy-5-fluoro-4,4-dimethoxy-1-oxopentan-3-aminium tartarate (10, R$^1$=ethyl, R$^2$=methyl, R$^6$=H)

A solution of ethyl 3-amino-5-fluoro-4,4-dimethoxypentanoate (1, R$^1$=ethyl, R$^2$=methyl 4.33 g, 19.4 mmol) in isopropanol (40 mL) was heated to 50° C., and treated with a solution of D,L-tartric acid (2.91 g, 19.4 mmol) in water (6.6 mL). The oil bath was removed and the mixture was stirred at ambient mixture for 2 h. The resulting suspension was diluted with a mixture of isopropanol (47 mL) and water (2 mL), and stirring was continued for further 2 h. The precipitate was filtered, washed with isopropanol (18 mL) and dried over $N_2$ purge to give the title compound (10, $R^1$=ethyl, $R^2$=methyl, $R^6$=H, 6.31 g, 87.1%). $^1$H NMR (500 MHz, CDCl$_3$) δ 4.58 (dd, J=11.0 and 46.5 Hz, 1H), 4.40 (dd, J=11.0 and 46.5 Hz, 1H), 4.09 (s, 2H), 4.04 (q, J=6.8 Hz, 2H), 3.44 (dd, J=3.1 and 10.4 Hz, 1H), 3.18 (s, 3H), 3.17 (s, 3H), 2.58 (dd, J=3.5 and 15.9 Hz, 1H), 2.29 (ddd, J=1.9, 9.8 and 15.9 Hz, 1H), 1.16 (t, 2.58, J=7.4 Hz, 3H).

INDUSTRIAL APPLICABILITY

The present invention relates to a method of producing a compound of formula 1. The method synthetic procedure does not require a very low temperature condition, and the intermediate 6 is easily purified via crystallization to provide high purity of the compound of formula 1 to render it to be more viable for a large scale of synthesis.

The invention claimed is:

1. A process for producing a compound of formula 6, which comprises the following steps:
   (a) preparing a compound of formula 4 by deprotecting a compound of formula 3;
   (b) preparing a compound of formula 9 by reacting the compound of formula 4 with $R^1OC(=O)OR^3$; and
   (c) reacting the compound of formula 9 with $NH(R^4)(R^5)$:

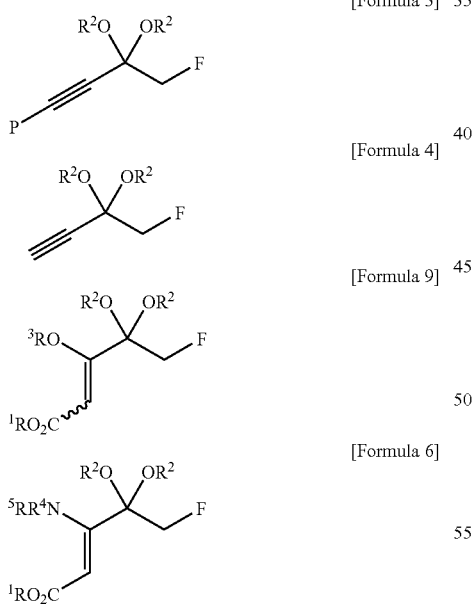

wherein,
$R^1$ and $R^3$ independently represent alkyl group;
$R^2$ independently represents alkyl group, or together with the oxygen atom to which they are attached may form a dioxolane or dioxane;
$R^4$ and $R^5$ independently represent hydrogen, trialkylsilyl group, arylmethyl group or 1-arylethyl group, and P represents protecting group.

2. The process according to claim 1, wherein the step (a) is carried out in the presence of one or more bases selected from the group consisting of $M^1OH$, $M^2(OH)_2$, $(M^1)_2CO_3$, $(M^1)HCO_3$ and $M^2CO_3$, wherein $M^1$ represents an alkali metal, and $M^2$ represents an alkaline earth metal.

3. The process according to claim 1, wherein the step (b) is carried out in the presence of one or more bases selected from the group consisting of primary, secondary or tertiary alkoxide of alkali metal, or alkaline earth metal; Grignard reagent; alkyllithium; lithium dialkylamide; lithium hexamethylsilazide; sodium hexamethylsilazide; and potassium hexamethylsilazide.

4. The process according to claim 3, wherein the amount of the base is 0.05 to 1.5 equivalents with respect to the compound of formula 4.

5. The process according to claim 1, wherein $R^1$ and $R^3$ of the step (b) are independently selected from the group consisting of methyl, ethyl, propyl, butyl and isopropyl.

6. The process according to claim 1, wherein the amount of $R^1OC(=O)OR^3$ in the step (b) is 1 to 5 equivalents with respect to the compound of formula 4.

7. The process according to claim 1, wherein the step (b) is carried out in one or more solutions selected from the group consisting of dimethylformamide, dimethylsulfoxide and N-methylpyrrolidinone, or a mixed solution with tetrahydrofuran thereof.

8. The process according to claim 1, wherein $R^4$ and $R^5$ in the step (c) are independently selected from the group consisting of hydrogen, trialkylsilyl, benzyl, 1-phenylethyl and 1-naphthylethyl.

9. The process according to claim 1, comprising another step after the step (c), wherein the compound of formula 6 is crystallized under one or more solvents selected from the group consisting of $C_1$-$C_5$-alcohol and $C_3$-$C_5$-ketone, and water.

10. The process according to claim 1, wherein the process for producing a compound of formula 3 comprises,
   (d) preparing a compound of formula 2 by reacting a compound of formula 8 with anion of trimethylsilylacetylene; and
   (e) reacting the compound of formula 2 with protecting group:

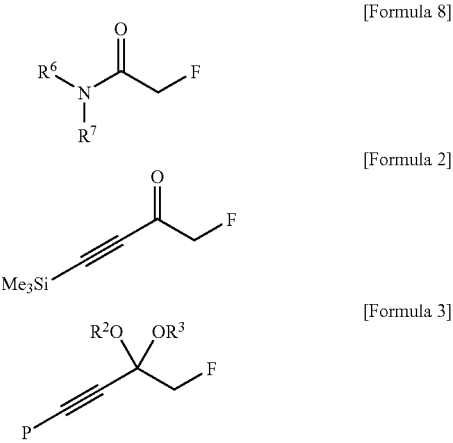

wherein,
$R^2$ independently represents alkyl group, or together with the oxygen atom to which they are attached may form a dioxolane or dioxane;

R⁶ and R⁷ independently represent alkyl group or alkoxy group, or together with the nitrogen atom to which they are attached may form a 4-8 membered heterocycle; and,
P represents protecting group.

11. The process according to claim 10, wherein the amount of anion of trimethylsilylacetylene in the step (d) is 1 to 3 equivalents with respect to the compound of formula 8.

12. A process for producing a compound of formula 1, which comprises the following steps:
(e) preparing a compound of formula 7 by reducing the compound of formula 6 obtained from the process according to claim 1 in the presence of a reducing agent capable of selectively reducing the double bond between carbons; and
(f) hydrogenating the compound of formula 7:

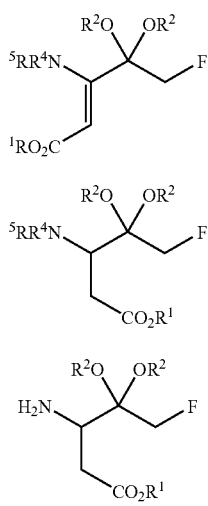

[Formula 6]

[Formula 7]

[Formula 1]

wherein,
R¹ represents alkyl group;
R² independently represents alkyl group, or together with the oxygen atom to which they are attached may form a dioxolane or dioxane; and,
R⁴ and R⁵ independently represent hydrogen, trialkylsilyl group, arylmethyl group or 1-arylethyl group.

13. The process according to claim 12, wherein the reducing agent of step (e) is selected from the group consisting of (i) sodium triacetoxyborohydride; (ii) acetic acid and sodium cyanoborohydride; of (iii) acetic acid and sodium borohydride.

14. The process according to claim 12, wherein the hydrogenation process is carried out under the presence of a metal catalyst in the step (f).

15. A process for producing a compound of formula 10, which comprises reacting the compound of formula 1 produced according to claim 12 with tartaric acid derivatives:

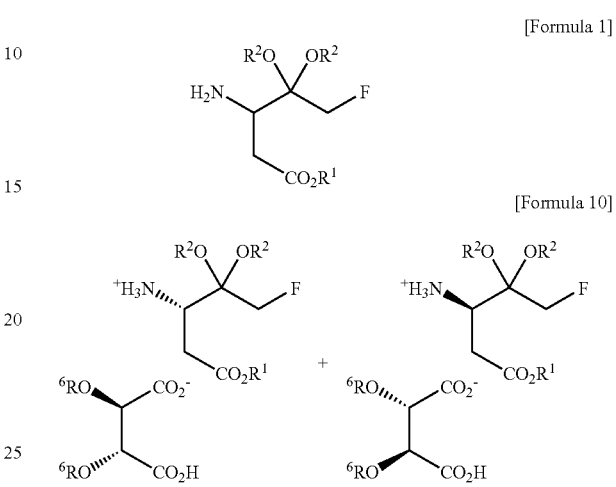

[Formula 1]

[Formula 10]

wherein,
R¹ represents alkyl group;
R² independently represents alkyl group, or together with the oxygen atom to which they are attached may form a dioxolane or dioxane;
R⁶ represents hydrogen, alkyl group or acyl group, wherein acyl group has a form of RC(═O)—, and,
R is alkyl group or aryl group.

16. The process according to claim 15, wherein the amount of tartaric acid derivatives is 0.9 to 1.5 equivalents with respect to the compound of formula 1.

17. The process according to claim 15, wherein the tartaric acid derivative is tartaric acid.

18. The process according to claim 15, wherein one type of stereoisomer in the compound of formula 10 is prepared by using optically active tartaric acid or O,O'-dibenzoyltartaric acid as the tartaric acid derivatives.

* * * * *